(12) United States Patent
Westbye

(10) Patent No.: US 9,550,027 B2
(45) Date of Patent: *Jan. 24, 2017

(54) TAMPER EVIDENT NEEDLE GUARD FOR SYRINGES

(71) Applicant: SAFETY SYRINGES, INC., Franklin Lakes, NJ (US)

(72) Inventor: Lars Tommy Westbye, Carlsbad, CA (US)

(73) Assignee: Safety Syringes, Inc., Franklin Lakes, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/108,231

(22) Filed: Dec. 16, 2013

(65) Prior Publication Data

US 2014/0228754 A1   Aug. 14, 2014

Related U.S. Application Data

(63) Continuation of application No. 12/947,724, filed on Nov. 16, 2010, now Pat. No. 8,608,693, which is a (Continued)

(51) Int. Cl.
*A61M 5/315* (2006.01)
*A61M 5/32* (2006.01)
(Continued)

(52) U.S. Cl.
CPC ........ *A61M 5/31511* (2013.01); *A61M 5/3243* (2013.01); *A61M 5/502* (2013.01);
(Continued)

(58) Field of Classification Search
CPC .................. A61M 5/31501; A61M 5/31511; A61M 5/3243; A61M 5/502; A61M 5/5086; A61M 5/3271; A61M 2005/3139
See application file for complete search history.

(56) References Cited

U.S. PATENT DOCUMENTS 3,820,652 A   6/1974   Thackston
5,120,309 A   6/1992   Watts
(Continued)

FOREIGN PATENT DOCUMENTS

WO   WO 93/02728 A1   2/1993
WO   WO 99/17823 A1   4/1999

*Primary Examiner* — Laura Bouchelle
*Assistant Examiner* — Justin L Zamory
(74) *Attorney, Agent, or Firm* — The Webb Law Firm

(57) ABSTRACT

A medicine injection device comprises a cartridge having a cartridge barrel and a plunger having a plunger shaft slidable within the cartridge barrel. The cartridge may have, e.g., a pre-filled medicine. The medicine injection device further comprises a body having a proximal end, a distal end, and a cavity in which the cartridge barrel is disposed. The proximal end of the body may optionally form a finger grip. The medicine injection device further comprises a plunger locking mechanism attached to the proximal end of the body. The plunger locking mechanism comprises a member with an aperture slidably engaged with the plunger shaft. The locking mechanism is configured for preventing the plunger from being removed from the cartridge barrel. For example, the plunger shaft may include a locking stop, e.g., a flange, that engages with the aperture in an interference arrangement.

10 Claims, 13 Drawing Sheets

Related U.S. Application Data continuation of application No. 10/373,531, filed on Feb. 24, 2003, now abandoned.

(51) Int. Cl.
 *A61M 5/50* (2006.01)
 *A61M 5/31* (2006.01)

(52) U.S. Cl.
 CPC ........ *A61M 5/5013* (2013.01); *A61M 5/5086* (2013.01); *A61M 5/3271* (2013.01); *A61M 2005/3139* (2013.01); *Y10T 29/4984* (2015.01)

(56) References Cited

U.S. PATENT DOCUMENTS

| | | |
|---|---|---|
| 5,242,416 A | 9/1993 | Hutson |
| 5,366,447 A | 11/1994 | Gurley |
| 5,373,590 A | 12/1994 | Svae et al. |
| 5,380,296 A | 1/1995 | Smedley et al. |
| 5,395,339 A * | 3/1995 | Talonn ............... A61M 5/31511 604/110 |
| 6,159,184 A | 12/2000 | Perez et al. |
| 6,186,980 B1 | 2/2001 | Brunel |
| 6,344,032 B1 | 2/2002 | Perez et al. |
| 6,416,323 B1 * | 7/2002 | Grenfell ............. A61M 5/3271 433/90 |
| 7,014,622 B1 | 3/2006 | Pressly, Sr. et al. |
| 2002/0068921 A1 | 6/2002 | McWethy et al. |
| 2002/0198499 A1 | 12/2002 | Hu |
| 2004/0167476 A1 * | 8/2004 | Westbye ...................... 604/192 |

\* cited by examiner

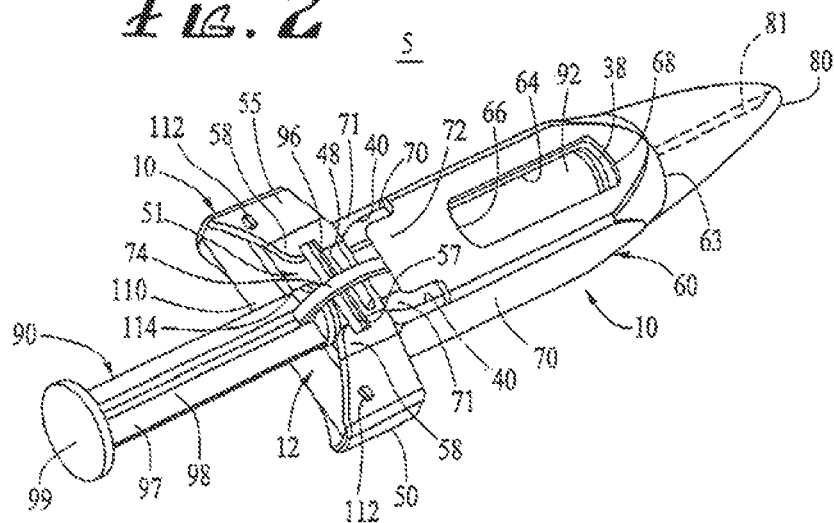
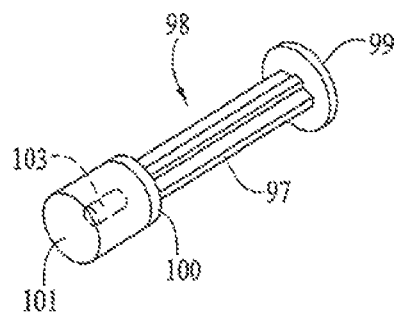
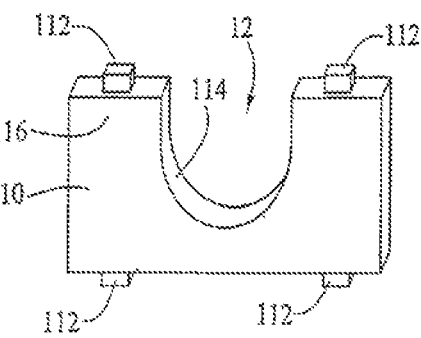

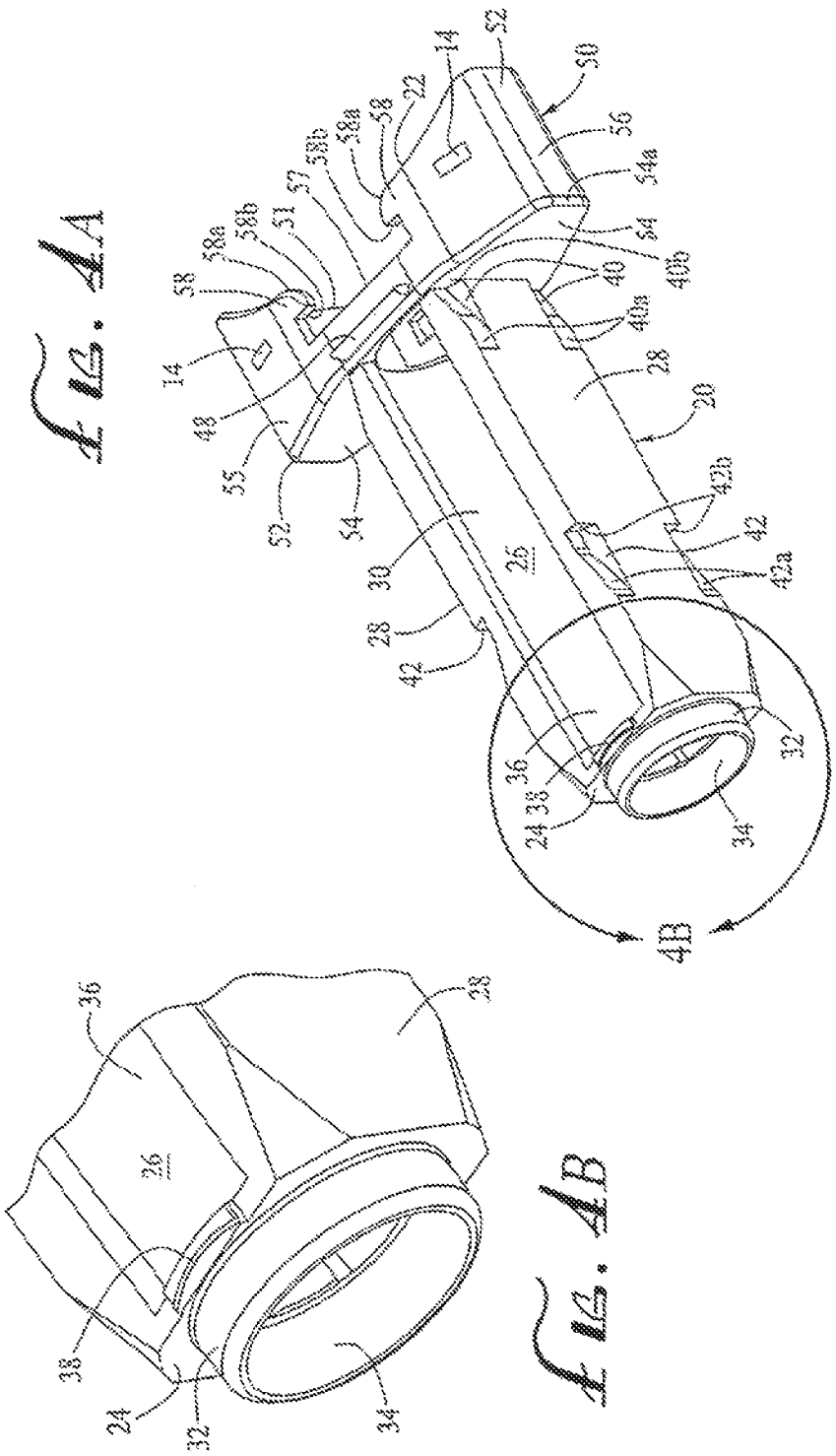

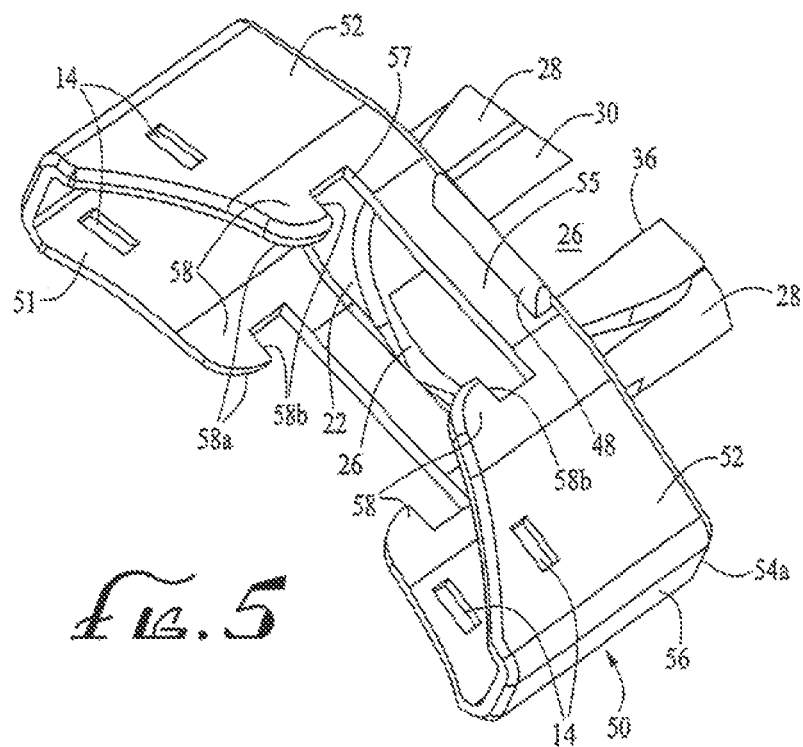

TAMPER EVIDENT NEEDLE GUARD FOR SYRINGES

CROSS-REFERENCE TO RELATED APPLICATIONS

This application is a continuation application of application Ser. No. 12/947,724 filed Nov. 16, 2010, now U.S. Pat. No. 8,608,693, which is a continuation application of application Ser. No. 10/373,531 filed Feb. 24, 2003, now abandoned, which applications are fully incorporated herein by reference.

FIELD OF THE INVENTION

The present invention relates generally to safety systems for syringes or other medical cartridges, and more particularly to a holder for a syringe that prevents removing or otherwise tampering with the contents of the syringe.

BACKGROUND

Medication is often dispensed using a medical cartridge, such as a syringe, having a barrel with a needle at one end and a plunger slidably inserted into the other end. Such cartridges are often referred to as "pre-filled syringes" because they may contain a specific dosage or volume of medication when they are initially provided, as compared to conventional syringes that are furnished empty and filled by the user.

Alternatively, a medical cartridge may be used, such as a vial or an ampule, that includes a penetrable seal instead of a needle on one end of the barrel, and/or a piston rather than a plunger on the other end.

Because of the threat of communicable disease, a number of syringes and adapters have been developed to prevent accidental needle sticks or inadvertent reuse of needle devices. Many of these devices, however, are not easy to use or are complicated to manufacture, resulting in a less effective disposable syringe or safety device.

Another consideration with unit dose cartridges is that they are often made from glass, particularly cartridges for holding certain vaccines or biotech drugs where concern about microorganisms or other contaminants is most critical. Glass cartridges are very fragile and often break during transportation or use. Some existing adapters may not adequately protect the cartridge contained therein from such risks. Others provide greater protection for the cartridge, but may obstruct the professional's view of the cartridge when the device is being used, hampering monitoring of the medication being delivered.

A further consideration with unit dose cartridges is that they are often filled with extremely expensive medications or drugs that sometimes cost as much as two thousand dollars per unit dose. The high cost of the medicine stored in these pre-filled syringes has created a valuable market for resale of the drugs and medications. Because of their value, individuals may be tempted to remove all or part of the expensive medication and replace it with a less expensive substitute.

Accordingly, a device that prevents tampering, or provides evidence of tampering, with a substance inside a pre-filled syringe would be considered useful.

SUMMARY OF THE INVENTION

The present inventions are directed to medicine injection devices, kits, and methods for preventing removal of a plunger from a cartridge.

In accordance with one aspect of the present inventions, a medicine injection device comprises a cartridge having a cartridge barrel and a plunger having a plunger shaft slidable within the cartridge barrel. The cartridge may be pre-filled with a medicine or drug. In this case, the medicine injection device can be fully assembled by a single entity with the pre-filled cartridge, or may be supplied to a drug manufacturer in kit form with an empty cartridge that is then filled with medicine and then assembled by the drug manufacturer. The medicine injection device further comprises a body having a proximal end, a distal end, and a cavity in which the cartridge barrel is disposed. The proximal end of the body may optionally form a finger grip.

By way of non-limiting example, the cartridge can be a syringe that comprises a needle that extends from the cartridge barrel. In this case, the medicine injection device can further comprise a shield that is slidably attached to the body between a retracted position for exposing the needle, and an extended position for substantially covering the needle. The shield can optionally be biased to slide towards the extended position by, e.g., utilizing a spring mechanism. The medicine injection device may further comprise a frangible cap attached to the shield for preventing access to the needle.

The medicine injection device further comprises a plunger locking mechanism attached to the proximal end of the body. The plunger locking mechanism comprises a member with an aperture slidably engaged with the plunger shaft. The locking mechanism is configured for preventing the plunger from being removed from the cartridge barrel. For example, the plunger shaft may include a locking stop, e.g., a flange, that engages with the aperture in an interference arrangement.

In the preferred embodiment, the plunger locking mechanism comprises a flange through which the aperture extends. The flange is mounted in the proximal end of the body, e.g., within a recess formed within the lateral surfaces of an optional finger grip. In this case, the body comprises at least one pair of opposing tab slots, and the flange may comprise at least one pair of opposing tabs mated within the opposing tab slots. To facilitate assembly of the medicine delivery device, the aperture may be formed on an edge of the flange, such that the plunger shaft can be laterally received within the aperture.

In accordance with another aspect of the present inventions, a method for assembling a medicine injection device comprises inserting a medical cartridge into a cavity of a body through a proximal end of the body. The method may include filling the medical cartridge with medicine.

By way of non-limiting example, the cartridge can be a syringe that comprises a needle that extends from the cartridge barrel. In this case, the method can further comprise attaching a shield to the body, the shield being slidable between a retracted position for exposing the needle, and an extended position for substantially covering the needle. The shield can optionally be biased to slide towards the extended position by, e.g., utilizing a spring mechanism. The method can further comprise attaching a frangible cap to the shield for preventing access to the needle.

The method further comprises attaching a plunger locking mechanism to the proximal end of the holder, wherein the plunger locking mechanism includes an aperture. The plunger locking mechanism may comprise a flange through which the aperture extends, in which case, the method may further comprise mounting the flange within the proximal end of the body. The preferred method may comprise mating at least one pair of opposing tabs within the proximal end of the body with at least one pair of opposing tabs of the flange. In the preferred method, the plunger shaft may be laterally received within the aperture, for example, if the aperture is formed on the edge of the flange.

The method further comprises receiving the plunger shaft within the aperture of the plunger locking mechanism to prevent removal of the plunger from the medical cartridge, while allowing the plunger shaft to slide within the aperture. For example, the plunger may comprise a locking stop, e.g., a flange, on the plunger shaft that engages the aperture of the locking mechanism when an attempt is made to remove the plunger from the medical cartridge.

BRIEF DESCRIPTION OF THE DRAWINGS

For a better understanding of the invention, and to show how it may be carried into effect, reference will be made, by way of example, to the accompanying drawings, in which:

FIG. 2 is another perspective view of the medicine injection device of FIG. 1;

FIG. 3 is a plunger used with the syringe of the medicine injection device of FIG. 1;

FIG. 4A is a perspective view of a body used in the medicine injection device of FIG. 1;

FIG. 4B is an enlarged view of the distal portion of the body of the medicine injection device of FIG. 4A;

FIG. 5 is a perspective view of a finger grip formed at the proximal end of the body of FIG. 4A;

FIG. 6 is a perspective view of a plunger locking mechanism used in the medicine injection device of FIG. 1;

DETAILED DESCRIPTION OF THE PREFERRED EMBODIMENTS

Figure 1:
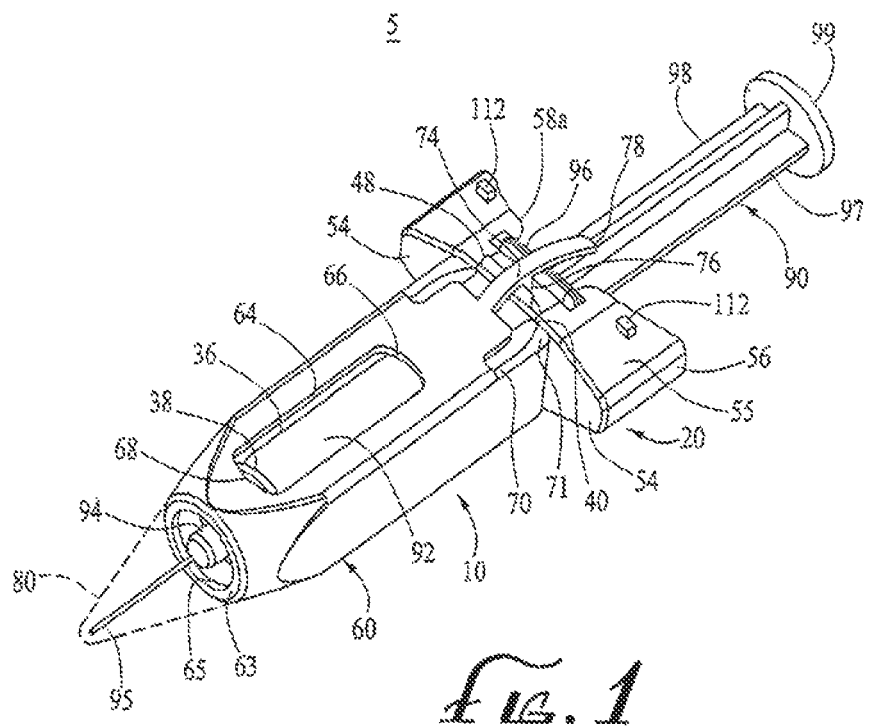
FIG. 1 is a perspective view of a medicine injection device constructed in accordance with a preferred embodiment of the present inventions.

Turning now to the drawings, FIGS. 1 and 2 illustrate a preferred embodiment of a medicine injection system 5 constructed in accordance with the present invention. The injection system 5 comprises a syringe 90 and a passive needle guard 10 for holding the syringe 90. Generally, the passive needle guard 10 includes four parts, namely a body 20 for receiving and holding the syringe 90, a shield 60 slidably attached to the body 20, a plunger locking mechanism 12 (FIG. 2), and a frangible cap 80 (FIG. 2). The body 20, shield 60, and locking mechanism 12 are generally molded from plastic, such as polypropylene, k-resin, or polycarbonate, and are preferably substantially clear and colorless to facilitate observation of the syringe 90 received therein. Alternatively they may be translucent or opaque, and may be colored, such as a latex color or a flesh tone.

Figure 15:
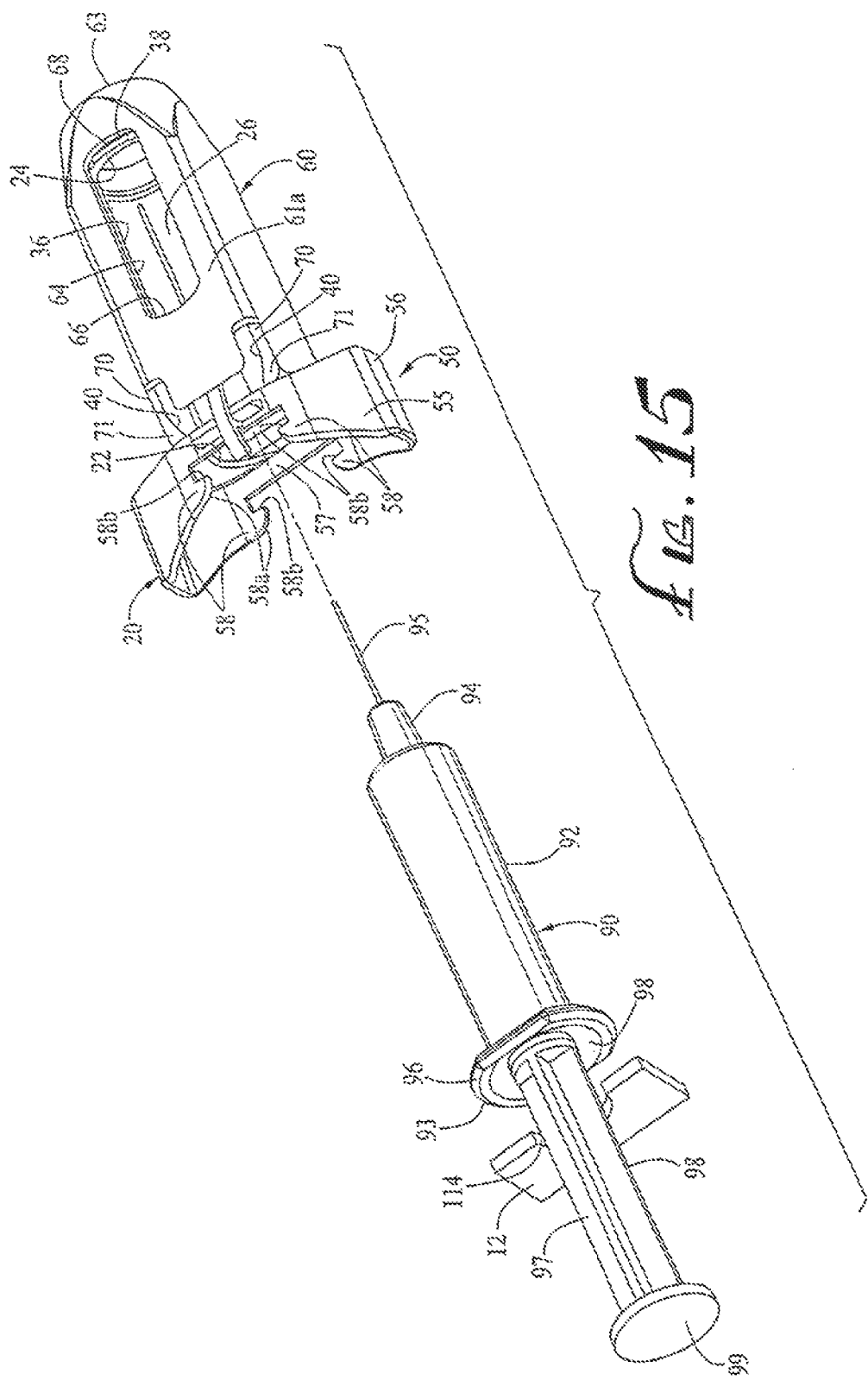
FIG. 15 is a perspective view of the pre-assembled medicine injection device of FIG. 1.

The preferred cartridge is a pre-filled syringe 90 that generally has a substantially smooth-walled cylindrical barrel 92, a distal end or hub 94 including a hypodermic needle 95, a frangible needle cover or cap 80, a proximal end 93 (FIG. 15) having a flange 96, and a plunger 98 that is inserted into the barrel 92 at the proximal end 93. The flange 96 may have a sufficiently large width to provide a finger grip for the syringe 90, or may simply be a small lip to facilitate manufacturing, for example, on a filling line.

As best seen in FIG. 3, the plunger 98 includes a shaft 97 having a thumb pad 99 on its proximal end and a flange 100 and a threaded tip 103 on its distal end. The plunger 98 further comprises a piston 101 that includes a threaded bore (not shown) that is adapted to screw onto the threaded tip 103 of the plunger shaft 97 and abut against the distal surface of the flange 100. In a preferred embodiment, the syringe 90 is filled with a predetermined dose of medication through the proximal end 93, and then the plunger 98 is slidably inserted into the proximal end 93 to substantially seal the barrel 92. Alternatively, other syringes or cartridges may be provided that include a seal (not shown) on the distal end instead of a distal hub 94 and needle 95.

Turning to FIGS. 4A, 4B and 5, the body 20 has opposing side rails 28 defining two elongate openings or windows 36 extending at least partially between a proximal end 22 and a distal end 24 of the body 20. The two side rails 28 generally have a "C" shape defining a cavity 26 extending axially from the proximal end 22 to the distal end 24 of the body 20. Alternatively, instead of the side rails 28, the body 20 may include a substantially rectangular body having four side walls (not shown). If a four-walled body is provided, it may be desirable to provide one or more elongate openings or windows in one or more of the side walls, preferably in two walls on opposite sides of the body 20.

The inside surfaces 30 of the rails 28 are preferably concave, conforming substantially to the outer diameter of a conventional pre-filled syringe 90. Alternatively, guide rails, resilient ribs, and the like (not shown) may be provided on the inside surface 30 to facilitate insertion of a cartridge into the cavity 26 and/or to provide lateral support for a syringe received therein. U.S. Pat. No. 6,344,032, issued to Perez et al., the disclosure of which is expressly incorporated herein by reference, discloses exemplary resilient rib structures that may be provided within the body 20. The outer surfaces of the side rails 28 define a substantially rectangular cross-section for the body 20, providing a substantially rigid structure for protecting the syringe 90 received within the body 20. Alternatively, outer surfaces of the side rails 28 may define other cross-sectional shapes, e.g., round or oval.

A substantially rigid collar 32 (FIG. 4A) is molded on the distal end 24 of the body, the collar 32 preferably having a substantially annular shape. The collar 32 defines an opening 34 for allowing a needle 95 and the frangible cap 80 on the syringe 90 (best seen in FIGS. 1 and 2) received in the cavity 26 to extend distally beyond the body 20. The opening 34 preferably has a diameter smaller than the cavity 26, such that the distal end 24 substantially retains the syringe inside the cavity 26 preventing distal movement. Alternatively, the distal end 24 may be tapered or otherwise partially obstructed for engaging the distal end of the syringe 90 and/or preventing distal movement of the syringe 90. Stop tabs 38 may be molded directly on the distal end 24 of the body 20, preferably on two opposite sides of the distal end 24, or alternatively, may be provided on a cantilever member (not shown), such as that disclosed in U.S. Pat. No. 6,030,366, issued to Mitchell, the disclosure of which is expressly incorporated herein by reference.

A finger grip 50 is molded on the proximal end 22 of the body 20, and includes a pair of wing-like members or flanges 52 generally defining a "T" shape. Each wing-like member 52 includes a distal surface or finger ledge 54, and an outer gripping surface 56 extending proximally from the outer edge 54a of the finger ledge 54. The outer gripping surface 56 may include a lip, grooves, or other irregularities (not shown) protruding radially from its proximal end or set in the surface 56, for example, to facilitate a user holding the finger grip 50. Lateral surfaces 55 extend proximally from the finger ledges 54 between the gripping surfaces 56, thereby defining a recess 51 communicating with the cavity 26 in the body 20. Alternatively, the recess 51 may be eliminated and/or the finger grip 50 may be shortened, for example, to simply be a flat transverse flange for accommodating shorter syringes or cartridges (not shown).

A catch or tab 48 may be molded or otherwise extend from one of and preferably both of the lateral surfaces 55 of the finger grip 50. Alternatively, the catch 48 may be provided on the proximal end 22 of the body 20 adjacent the finger grip 50 (not shown). The catch 48 engages the tabs 76 on the latch members 74 as described further below.

In a preferred embodiment, a locking mechanism is provided on the finger grip 50 and/or on the proximal end of the body 20 for engaging a flange 96 of the syringe 90 (best seen in FIGS. 1 and 2) received in the cavity 26, and thereby substantially securing the syringe within the body 20. Preferably, the locking mechanism includes a plurality of locking detents 58 at least partially defining an aperture or slot 57 that are formed in lateral surfaces 55 of the finger grip 50 for receiving the flange 96 therein. Alternatively, other locking mechanisms may be provided on the proximal end 22 of the body 20, such as those disclosed in U.S. Pat. No. 6,344,032, the disclosure of which has been previously incorporated herein by reference. In a further alternative, other known mechanisms may be used to secure a syringe within the body 20, such as locking detents or a collet mechanism (not shown) on the distal end 24 of the body 20.

One or more sets of detent pockets may be molded into the body 20 to facilitate securing the relative movement of the shield 60 and body 20. In a preferred embodiment, a set of proximal detent pockets 40 is provided adjacent the finger grip 50, and a set of distal detent pockets 42 is provided at a more distal location on the body 20. Preferably, the proximal detent pockets 40 have sloping distal edges 40a and substantially blunt proximal edges 40b. The distal detent pockets 42 also have substantially blunt, and preferably oblique, proximal edges 42b.

One or more sets of tab openings 14 are molded into the body 20 to facilitate securing the plunger locking mechanism 12 to the body 20, as will be described in further detail below. In a preferred embodiment, the tab openings 14 are molded into the lateral surfaces 55 of the finger grip 50.

Referring to FIGS. 2, 5 and 6, in the illustrated embodiment, the plunger locking mechanism 12 comprises a semi-rigid flange 110 mounted within the recess 51 of the finger grip 50. The shape of the flange 110 conforms to the shape of the recess 51, such that it fits snugly within the finger grip 50. The locking mechanism 12 further comprises tabs 112 that mate with corresponding tab openings 14 on the finger grip 50. The locking mechanism 12 further comprises an aperture 114 formed within the flange 110 for receiving the shaft 97 of the plunger 98. In the illustrated embodiment, the aperture 114 is formed on an edge 116 of the flange 110, such that the flange 110 has a C-shape. As will be described in further detail below, this facilitates the assembly process by allowing the locking mechanism 12 to laterally receive the shaft 97 of the plunger 98.

Figure 7:
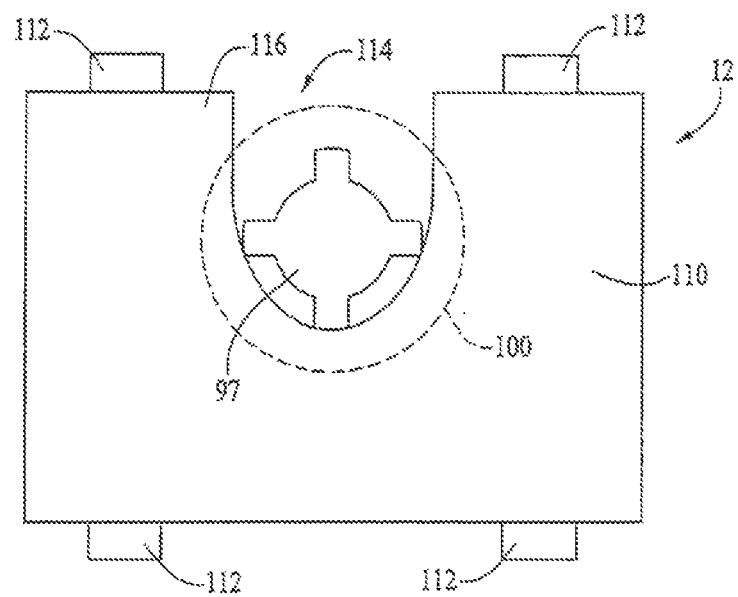
FIG. 7 is a plan view of the plunger locking mechanism of FIG. 6, particularly showing a plunger shaft received by the plunger locking mechanism.

The aperture 114 is configured to allow the plunger 98 to slide within the cavity 26 of the body 20, while preventing the plunger 98 from being entirely removed from the syringe 90. Specifically, the flange 100 at the distal end of the plunger shaft 97 serves as a stop that engages with the sides of aperture 114 in an interfering arrangement when an attempt is made to pull the plunger 98 out of the body cavity 26. In the illustrated embodiment, the diameter of the plunger shaft 97 is less than the diameter of the plunger flange 100. The aperture 114, which is semi-circular or oval, has a diameter that is greater than the diameter of the plunger shaft 97, thereby allowing the plunger 98 to slide relative thereto, but less than diameter of the plunger flange 100 (shown in dashed lines in FIG. 7), thereby preventing the plunger 98 from being pulled through the aperture 114. Thus, the plunger locking mechanism 12 prevents the removal of the plunger 98 from the pre-filled syringe 90, thereby preventing access to the contents of the syringe 90 via the open end of the syringe 90 and the resultant tampering of medication or drugs in the syringe 90.

Figure 8:
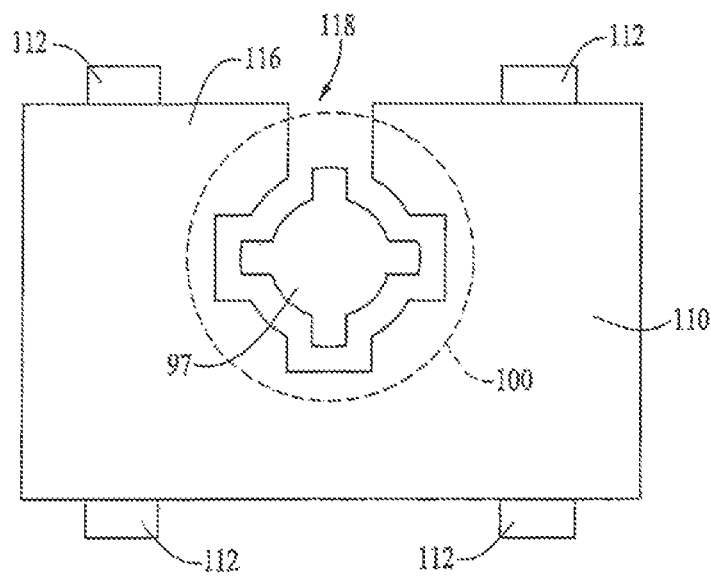
FIG. 8 is a plan view of a modified embodiment of the plunger locking mechanism of FIG. 6, particularly showing a plunger shaft received by the plunger locking mechanism.
Figure 9:
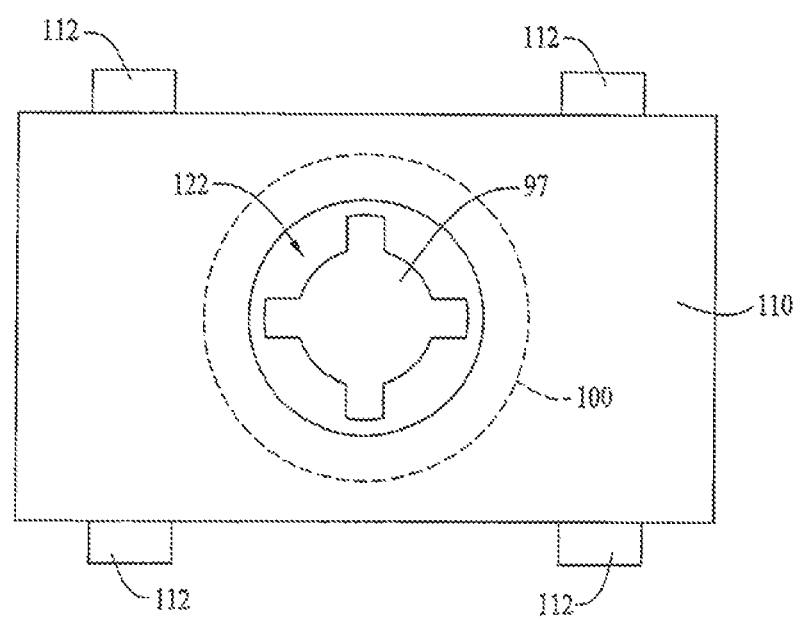
FIG. 9 is a plan view of another modified embodiment of the plunger locking mechanism of FIG. 6, particularly showing a plunger shaft received by the plunger locking mechanism.

It should be noted that although the aperture is semi-circular or oval, other cross-sectional shapes can be used. For example, FIG. 8 illustrates an aperture 118 that has a cross-sectional profile in the shape of a cross, which matches the cross-sectional shape of the plunger shaft 97, thereby allowing it to slide relative thereto, while preventing the circular plunger flange 100 from being pulled through it. In this case, the flange 110 can be twisted to allow lateral receipt of the plunger shaft 97 during assembly. It should also be noted that in certain arrangements, the apertures 114/118 need not be situated on the edge 116 of the flange 100. For example, FIG. 9 illustrates a closed circular aperture 122. In this case, if the plunger flange 100 is removably attached to the plunger shaft 97, e.g., via a threaded engagement, the plunger shaft 97 can be axially received through the closed aperture 122 before these components are attached to the plunger shaft 97.

Figure 10:
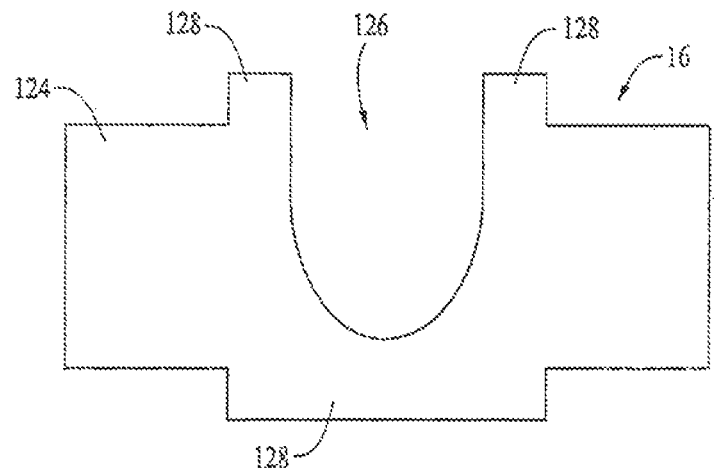
FIG. 10 is a plan view of another plunger locking mechanism used in the medicine injection device of FIG. 1.
Figure 11:
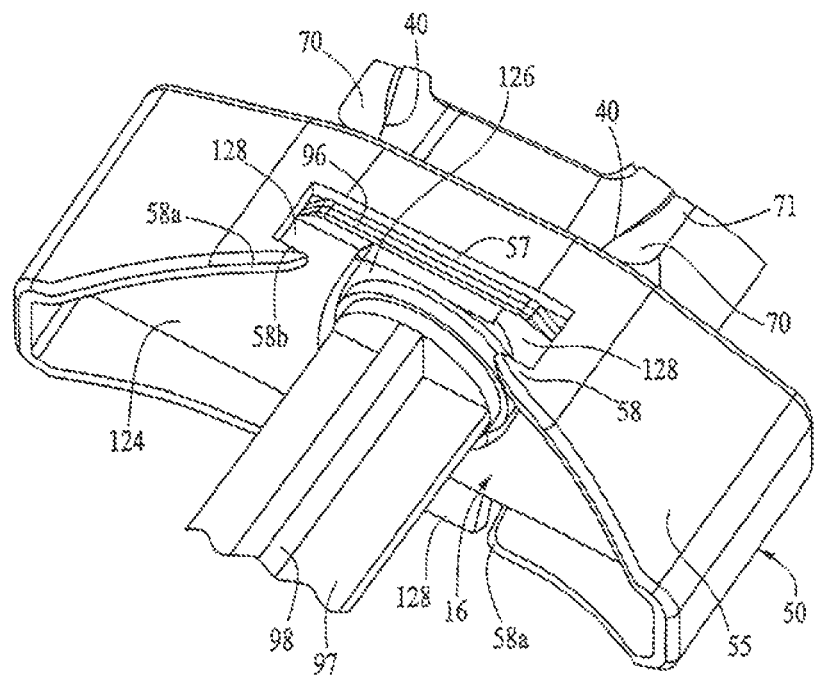
FIG. 11 is a perspective view of the proximal end of the medicine injection device of FIG. 1.

Alternative embodiments of other plunger locking mechanisms and their arrangement with the body 20 are contemplated by the present inventions. For example, FIGS. 10 and 11 illustrate a plunger locking mechanism 16 that can be mounted within the slot 57 of the finger grip 50. The locking mechanism 16 comprises a flange 124 and an aperture 126 formed through the flange 124. As with the previously described aperture 114, the aperture 126 is configured to laterally receive the shaft 97 of the plunger 98. The flange 124 comprises opposing tabs 128 that snugly fit within the opposing slots 57 between the flange 96 of the syringe 90 (when mounted within the slot 57) and the blunt distal edges 58b of the locking detents 58. Thus, the plunger locking mechanism 16 prevents the removal of the plunger 98 from the syringe 90, thereby preventing access to the contents of the syringe 90 via the open end of the pre-filled syringe 90 and the resultant tampering of medication or drugs in the pre-filled syringe 90.

Figure 12:
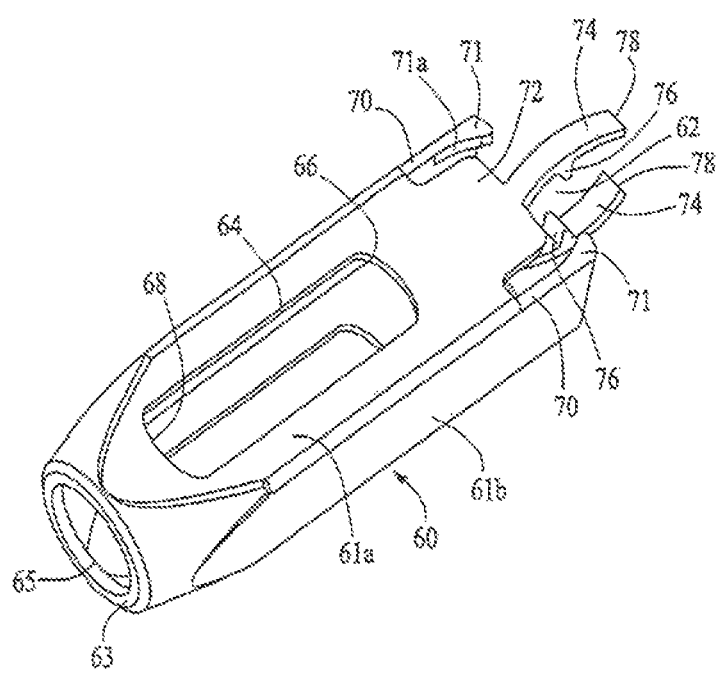
FIG. 12 is a perspective view of a shield used in the medicine injection device of FIG. 1.
Figure 13:
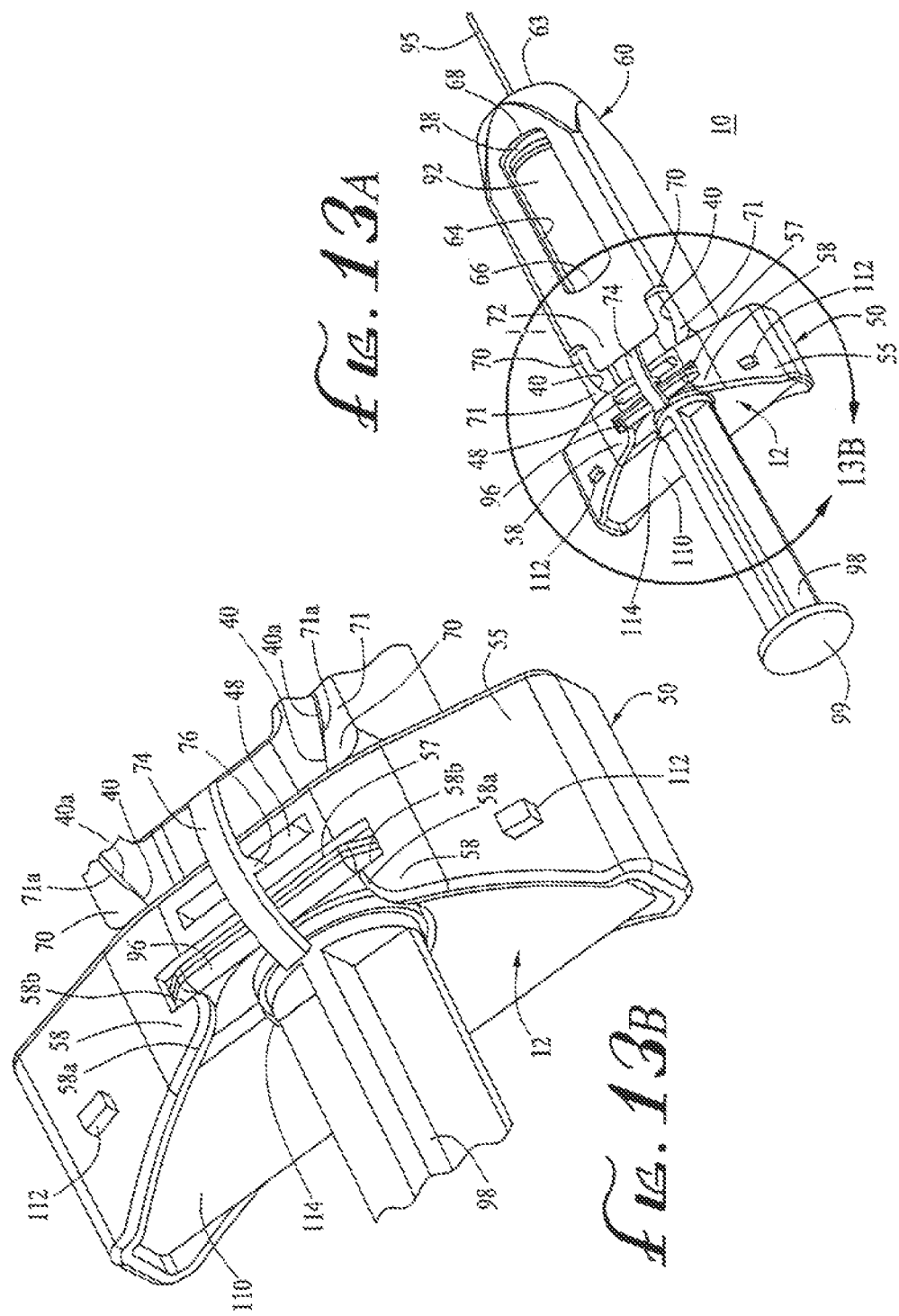
FIG. 13A is a perspective view of the medicine injection device of FIG. 1, particularly shown in a retracted state.
FIG. 13B is an enlarged view of the proximal end of the medicine injection device of FIG. 13A.

Turning to FIG. 12, the shield 60 is a tubular member adapted to slidably fit on the body 20, preferably having a substantially rectangular interior shape that conforms to the exterior shape of the body 20. The shield 60 includes four side walls 61a, 61b, an open proximal end 62, and an open distal end 63. The shield 60 and body 20 are slidable in relation to one another between an unguarded post, when the needle 95 is exposed (FIG. 13A), and a guarded post, when the needle 95 is substantially covered (FIG. 14A), as explained in further detail below.

One or more latch members or fingers 74 extend proximally from the shield 60, preferably molded to each of the assembly tabs 72. Alternatively, the latch members 74 may be made as separate pieces that are bonded or otherwise attached to the shield 60, for example, to the outside of the assembly tabs 72, using an adhesive and the like. Each latch member 74 includes an inwardly disposed catch or tab 76 located on an intermediate portion of the latch member 74 between the assembly tab 72 and a tip 78 of the latch member 74. The latch members 74 are preferably provided from a substantially flexible material such that they are resiliently deflectable for deflecting the intermediate portion radially outward, and thereby disengaging the catch 76 from the mating catch 48 on the body 20, but are biased to return inwards to promote engagement with the mating catches 48 on the body 20, as described further below.

A plurality of detent arms 70, preferably in opposing pairs, and a plurality of detents 71 are integrally molded directly onto or otherwise attached to the side walls 61b. The detents 71 preferably have shapes corresponding substantially to the shapes of the detent pockets 40, 42 in the body 20. Distal edges 71a of the detents 71 are preferably ramped to facilitate slidable engagement with the distal surfaces 40a of the proximal detent pockets 40. Proximal edges 71b (FIG. 14B) of the detents 71 are substantially blunt, and preferably oblique, for positively engaging the proximal edges 42b of the distal detent pockets 42 and locking the shield 60 in an extended position, as described further below. Additional information on detents and detent pockets for use with the present invention are described in the Mitchell patent referenced above. In addition, the detent arms 70 may include indents (not shown) for controlling the flexural strength of the detent arms 70, as the arms 70 may vary in size and thickness in embodiments adapted to accommodate a variety of syringes.

At least one wall 61a, and preferably the two opposite walls 61a, include an elongate opening or window 64 therethrough. The windows 64 may facilitate observation of the syringe 90 received in the body 20, and also provide a traveling slot for the stop tabs 38 on the body 20. The windows 64 have a proximal edge 66 and a distal edge 68 defined by the wall 61a that limit the relative movement of the shield 60 to the body 20, as explained below. Alternatively, the windows 64 may be divided by a cross-member (not shown) molded into the wall 61a that extends transversely across the window 64 if it is desired to further limit movement of the shield 60.

Optionally, the side walls 61a, 61b may include wings, a ring, or similar finger holds (not shown) extending radially from the shield 60 to ease movement of the shield 60 in relation to the body 20. In addition, the side walls 61a, 61b may provide a flat surface onto which a label may be applied, for example to identify the drug, medication, or other fluid contained within the pre-filled syringe 90 received within the guard 10, or an embossed pattern may be molded, possibly including a name or a logo.

The shield 60 has a distal opening 65 through which the distal hub 94 of the syringe 90 and needle 95 extend. The distal opening 65 is generally circular and has a diameter larger than that of the needle 95 on the syringe 90, and may be provided with a variety of diameters, for example, larger than the cartridge barrel 92 and/or hub 94, or configurations to facilitate use of the syringe 90. For example, the diameter of the opening 65 may be sufficiently large to accommodate a luer adapter (not shown) or other alternative distal tip to be provided on the syringe 90 or attached to the hub 94. Most preferably, the opening 65 has a diameter sufficiently small to minimize the risk of accidental sticks, for example, to prevent a finger from being directed into the shield 60 after use.

A spring mechanism (not shown) may be coupled to the body 20 and the shield 60 to bias the shield 60 towards an extended position. U.S. patent application Ser. No. 09/566,224, filed May 5, 2000, the disclosure of which is expressly incorporated herein by reference, describes various spring arrangements that can be incorporated into the guard 10.

Referring back to FIGS. 1 and 2, the cap 80 is frangibly attached to or otherwise extends from the distal end 63 of the shield 60 to prevent access to the contents of the syringe 90 and/or prevent exposing the needle 95 of the syringe 90. In a preferred embodiment, the cap 80 is attached by a weakened region 81 (shown in FIG. 2), which may be a perforated seam or otherwise a relatively thin region that extends from a distal end of the cap 80 to a proximal end of the cap 80. In the preferred embodiment, the cap 80 and shield 60 may be molded as a single piece with a weakened region 81 between them. In any event, the weakened region 81 preferably allows for quick, easy, and clean break away of the cap 80 from the shield 60, while preventing the cap 80 from being reattached to the shield 60. Thus, this arrangement will provide an immediate and easily recognizable indication that the cap 80 has been removed from the assembly, thereby preventing undetected access to the contents of the syringe 90 and the resultant tampering of medication or drugs in the pre-filled syringe 90 via the needle 95.

Referring to FIGS. 12, 13A and 13B, the passive needle guard 10 is generally provided to the user with body 20, shield 60, plunger locking mechanism 12, and frangible cap 80 (not shown). In the retracted position, the tabs 76 on the latch members 74 substantially engage the mating catches 48 on the body, thereby securing the shield 60 in the retracted position against the bias provided by a spring mechanism such as disclosed in U.S. patent application Ser. No. 09/724,657, filed Nov. 28, 2000, the disclosure of which is expressly incorporated herein by reference. In addition, the detents 71 may be received in the proximal detent pockets 40, thereby providing additional security to hold the shield 60 in the retracted position. Alternatively, the proximal detent pockets 40 may be used merely to receive the detents 71 and thereby allow the detent arms 70 to return to a relaxed state, rather than extending outward along the outer surface of the body 20. In a further alternative, the proximal detent pockets 40 may not be needed and may be eliminated.

Referring to FIGS. 4A and 12, to assemble the passive needle guard 10, the distal end 24 of the body 20 is inserted into the open proximal end 62 of the shield 60, with the window 36 in the body 20 aligned with the side wall 61a of the shield 60 having the window 64 therein. A spring (not shown) may be positioned within a passage and/or secured to the body 20 and shield 60 in a conventional manner. As the body 20 is inserted, the stop tab 38 engages a tapered interior edge (not shown) of the assembly tab 72 on the shield 60, allowing the stop tab 38 to pass under the side wall 61a. After the stop tab 38 passes under the side wall 61a, it may enter the window 64 where it may freely travel.

The stop tab 38 and window 64 cooperate to allow the shield 60 to slidably move in relation to the body 20, but substantially define the limits of their relative movement. The shield 60 may slide proximally and distally until the stop tab 38 abuts a distal edge 68 and a proximal edge 66 of the window 64, respectively. Specifically, when the stop tab 38 engages the distal edge 68 of the window 64, the shield 60 is in the retracted or unguarded position (FIG. 13A). When the stop tab 38 engages the proximal edge 66 of the window 64, the shield is in the extended or guarded position (FIG. 14A).

While the stop tab 38 and window 64 cooperate to limit the movement of the shield 60, the catches 48, 76, and the cooperating detents 71 and detent pockets 40, 42 on the shield 60 and body 20 also cooperate to hold the shield 60 either in the retracted position or in the extended position. During assembly, the latch members 74 may be deflected radially outwardly to avoid contact between the catches 76 thereon and the mating catches 48 on the body 20. Similarly, the detent arms 70 may be deflected radially outwardly such that the detents 71 do not engage the distal detent pockets 42 while the shield 60 is directed to the retracted position.

As best seen in FIGS. 13A and 13B, once the shield 60 is fully retracted, the latch members 74 and the detent arms 70 are released, whereupon they resiliently return inward such that the catches 76 on the latch members 74 engage the mating catches 48 on the body 20, and the detents 71 engage the proximal detent pockets 40. In the retracted position, the stop tab 38 also abuts the distal edge 68 of the window 64, thereby preventing further proximal movement of the shield 60. The sloping distal edges 71a of the detents 71 engage the sloping distal edges 40a of the proximal detent pockets 40 on the body 20, thereby assisting the cooperating catches 48, 76 in preventing the shield 60 from moving distally. However, the frictional resistance between the sloping distal edges 71a, 40a of the detents 71 and the proximal detent pockets 40 may be overcome by a distal force, such as that provided by the spring mechanism when the catches 48, 76 are released, as described further below. In addition, the slope of the sloping edges 40a, 42a may be adjusted to increase or decrease the frictional resistance, for example, to slow the shield 60 down when it initially advances from the retracted position.

Once assembled, the passive needle guard 10 is ready to receive a cartridge, such as the pre-filled syringe 90. The syringe 90 is preferably pre-assembled within the passive needle guard 10 before being furnished to a user, for example, at the time of manufacturing the passive needle guard 10. In a preferred embodiment, the syringe 90 may be pre-assembled by measuring out a dose of medication into the syringe 90, and then placing the plunger 98 within the barrel 92 of the syringe 90. Although the syringe 90 shown is the preferred medication delivery system that may be used with the passive needle guard 10, it will be appreciated that the passive needle guard 10 may be modified for use with other pre-filled or unit dose delivery systems, and that the term cartridge may include other such known systems. For example, the finger grip 50 on the proximal end 22 of the body 20 may be replaced with a plunger and plug assembly (not shown), such as that disclosed in U.S. Pat. No. 5,624,400, issued to Firth et al., the disclosure of which is expressly incorporated herein by reference. In addition, the collar 32 on the distal end 24 of the body 20 may be replaced with a double-ended needle cannula, such as that disclosed in the Firth et al. patent.

The distal end or hub 94 of the syringe 90 is inserted into the recess 51 of the finger grip 50 and the open proximal end 22 of the body 20 until it enters the cavity 26 and progresses distally towards the distal end 24 of the body 20. Once fully encapsulated, the distal end 94 of the syringe 90 may simply abut the distal end 24 of the body 20, or alternatively the distal end 94 may partially enter the opening 34 and engage the collar 32, thereby providing additional protection from lateral movement of the syringe 90.

Before the syringe 90 is inserted into the body 20 or before the flange 96 contacts the latch members 74, the latch members 74 may be deflected radially outward, while securing the shield 60 in the retracted position, for example, manually or in a jig or other mechanism. Thus, any contact between the latch members 74 and the syringe 90 may be avoided until the flange 96 passes the tips 78 of the latch members 74 and enters the recess 51 of the finger grip 50. The latch members 74 may then be released such that the catches 76 again engage the mating catches 48 on the body 20.

Alternatively, the syringe 90 may be inserted into the body 20 while the shield 60 is extended and the latch members 74 are consequently positioned distally away from the recess 51 into which the syringe 90 is to be inserted. Once the syringe 90 is fully inserted, the detents 71 may be disengaged from the distal detent pockets 42 and the shield 60 may be directed to the retracted position. In another alternative embodiment, an intermediate stop (not shown) may be provided to hold the shield 60 in a position between the extended and retracted positions, wherein the latch members 74 may be located distally away from the recess 51 into which the syringe 90 is to be inserted. Once the syringe 90 has been inserted, the shield may be directed to the retracted position where the catches 48, 76 may engage each other. The intermediate stop may then be disabled, for example, by being deflected or broken off, thereby preventing the intermediate stop from subsequently interfering with advancement of the shield 60 from the retracted position to the extended position.

Referring further to FIGS. 1 and 2, as the syringe 90 becomes fully encapsulated within the cavity 26, the flange 96 of the syringe 90 contacts the locking detents 58 on the finger grip 50. The locking detents 58 have tapered proximal edges 58a, allowing the syringe 90 to be directed further distally, the flange 96 moving the locking detents 58 aside and entering the slot 57. The locking detents 58 have substantially blunt distal edges 58b that prevent the syringe 90 from being removed proximally from the slot 57, thereby substantially permanently locking the syringe 90 into the body 20, and preventing axial (i.e. proximal and/or distal) movement of the syringe 90 within the passive needle guard 10.

Once the syringe 90 is locked into the passive needle guard 10, the needle 95 and its cap 80 extend through the opening 34 on the collar 32 and the opening 65 on the distal end 63 of the shield 60. Preferably, the length of the shield 60 is substantially coextensive with the barrel 92 of the syringe 90, allowing the needle 95 to extend beyond the distal end 63 of the shield 60, but protecting the hub 94 of the pre-filled syringe 90.

Figure 16:
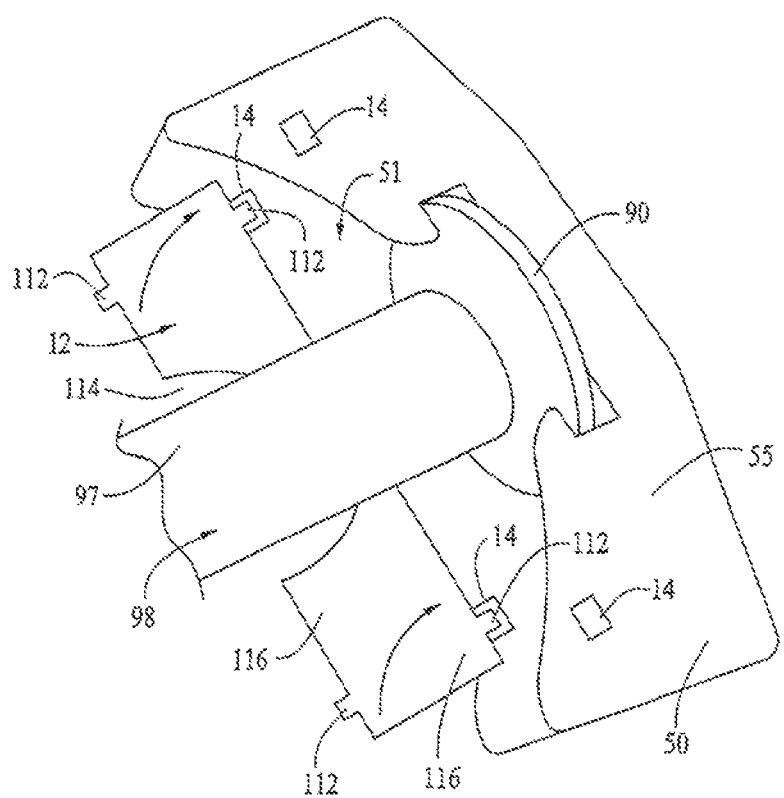
FIG. 16 is a plan view of a pre-assembled plunger locking mechanism used in the medicine injection device of FIG. 1.

Once the syringe 90 is firmly received into the guard 10, the plunger locking mechanism 12 is mounted within the recess 51 of the finger grip 50 and is placed into a locking arrangement with the plunger 98 to prevent removal of the plunger 98 from the syringe 90. Specifically, the plunger shaft 97 is laterally received within the aperture 114 of the locking mechanism 12, and the tabs 112 on one edge 116 of the flange 110 are inserted into the mating tab openings 14 within the lateral surface 55 of the finger grip 50, as illustrated in FIG. 16. With the plunger shaft 97 still received within the aperture 114 of the locking mechanism 12, the other edge 116 of the flange 110 is then distally rotated around the hinge formed by the already mated tabs 112 and tab openings 14 until the tabs 112 on the other edge are inserted into the mating tab openings 14 within the other lateral surface 55 of the finger grip 50. In this manner, the plunger 98 will be locked within the syringe 90.

Figure 17:
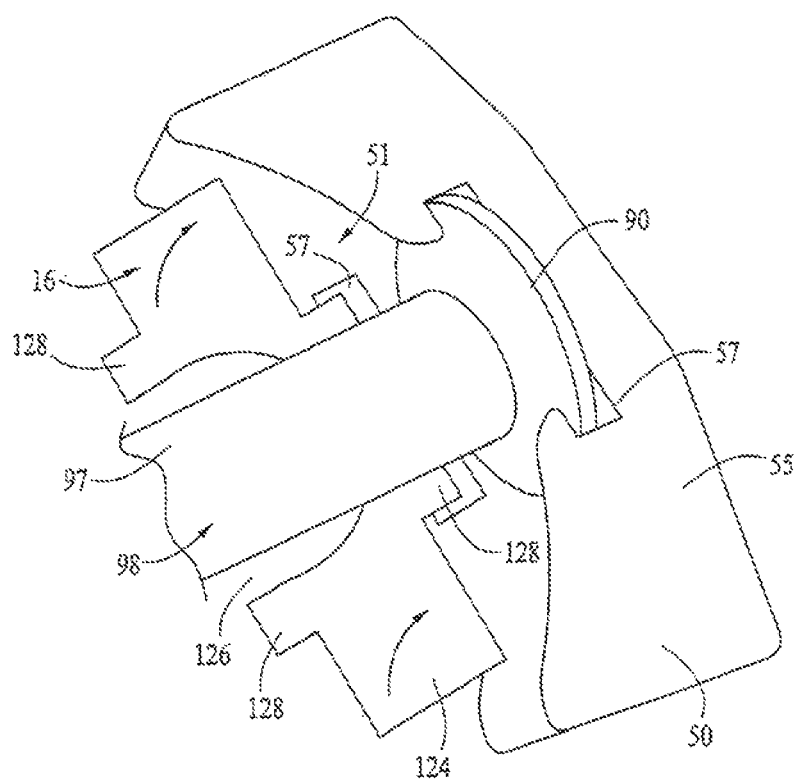
FIG. 17 is a plan view of another embodiment of a pre-assembled plunger locking mechanism used in the medicine injection device of FIG. 1.

In the case of the locking mechanism 16, the plunger shaft 97 is laterally received within the aperture 114 of the locking mechanism 12, and one of the tabs 128 of the flange 124 is inserted into the corresponding slot 57 within the lateral surface 55 of the finger grip 50, as illustrated in FIG. 17. With the plunger shaft 97 still received within the aperture 126 of the locking mechanism 16, the other tab 128 of the flange 124 is then distally rotated around the hinge formed by the already mated tab 124 and slot 57 until the other tab 112 is inserted into the opposite slot 57 within the other lateral surface 55 of the finger grip 50. In this manner, the plunger 98 will be locked within the syringe 90.

Returning to FIGS. 13 and 14, the syringe 90 encapsulated within the passive needle guard 10 may then be used in a conventional manner to deliver medication in the barrel 92. The needle cap 80 (shown in FIGS. 1 and 2) is first removed from the distal end 63 of the shield 60 by tearing or breaking the cap 80 away from the shield 60 at the weakened region 81. The needle 95 may then be inserted into the patient (not shown), and the medication delivered by depressing the plunger 98 distally. As may be seen from FIG. 1, the windows 64, 36 may facilitate observation of the barrel 92 of the syringe 90, allowing the user to monitor delivery of the medication therein.

The plunger 98 may be depressed until the thumb pad 99 contacts the tips 78 of the latch members 74. As the plunger 98 is depressed further, the thumb pad 99 causes the latch members 74 to compress axially and thereby deflect radially outwardly until the catches 76 are disengaged from the mating catches 48 on the body 20.

Figure 14:
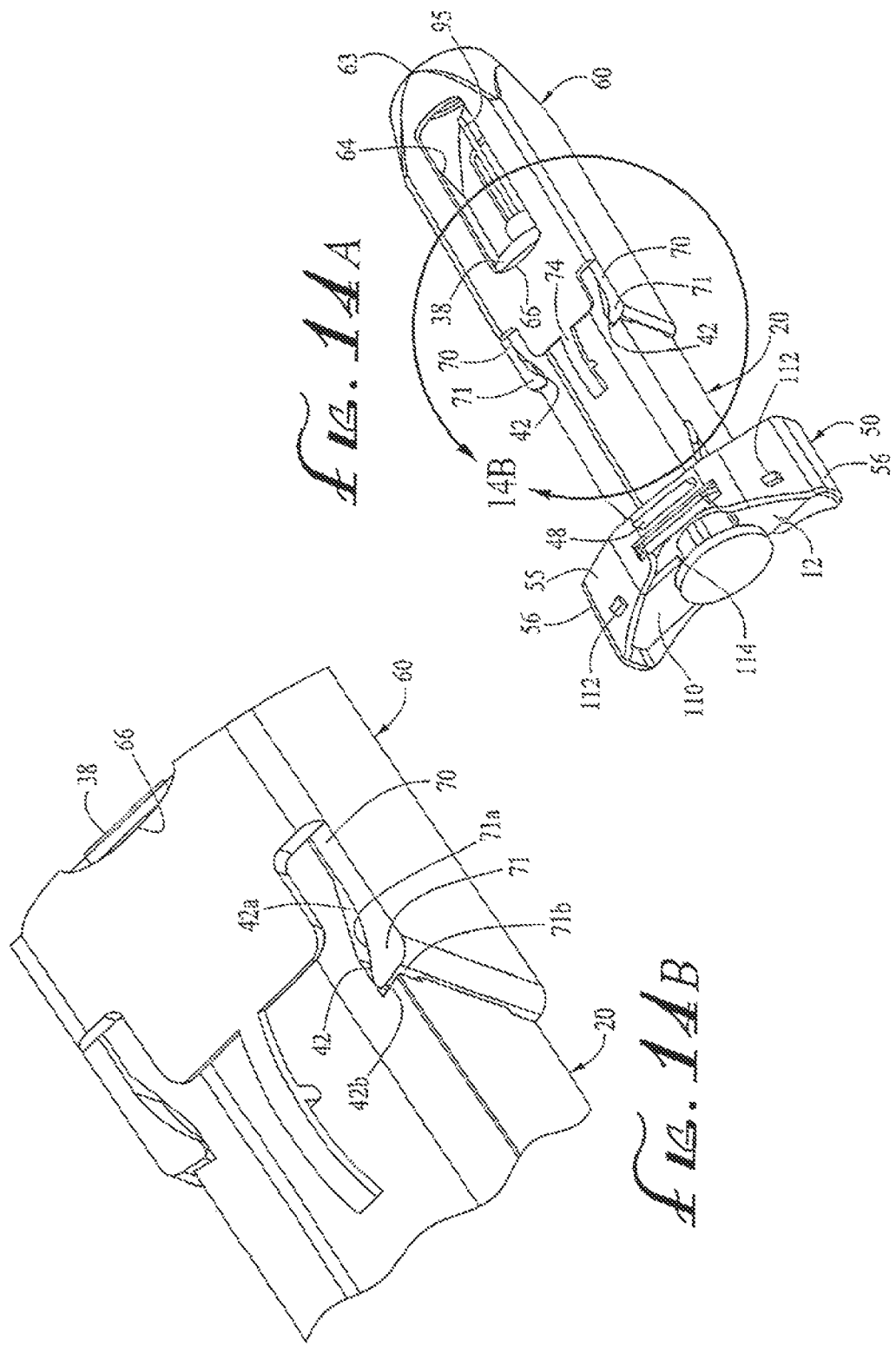
FIG. 14A is a perspective view of the medicine injection device of FIG. 1, particularly shown in an extended state.
FIG. 14B is an enlarged view of an intermediate region of the medicine injection device of FIG. 14A.

With the catches 48, 76 disengaged, the spring mechanism biases the shield 60 distally, whereupon the shield 60 may automatically advance towards the extended position, shown in FIG. 14. The latch members 74 merely slide along the body 20 as the shield 60 advances. Thus, the shield 60 may be automatically activated and advanced without requiring any action from the user other than depression of the plunger 98. Because of the predetermined location of the distal detent pockets 42, when the stop tab 38 reaches the proximal edge 66 of the window 64, the detents 71 substantially simultaneously enter the distal detent pockets 42. The blunt or oblique proximal edges 71*b* of the detents 71 engage the similarly shaped proximal edges 42*b* of the distal detent pockets 42, thereby preventing the shield 60 from being moved proximally. In an alternative embodiment, the body 20 may include pockets (not shown) for receiving the catches 76 on the latch members 74 when the shield 60 reaches the extended position, thereby further securing the shield 60 from proximal movement. Furthermore, because the stop tab 38 abuts the proximal edge 66 of the window 64, the shield 60 may not be moved further distally. Thus, the shield 60 is thereby substantially permanently locked in the extended position.

As the shield 60 advances to the extended position, the distal end 63 of the shield 60 passes over the needle 95, covering the needle 95. Once the shield 60 is locked in the extended position, the needle 95 may no longer be accessible, thereby substantially eliminating the risk of accidental sticks, and preventing reuse of the syringe 90. The guard 10 and syringe 90 may then be disposed of in a conventional manner.

A useful feature of the passive needle guard 10 is that the latch members 74 and/or the plunger 98 have predetermined relative lengths to activate the shield 60 at a desired time during the plunger stroke. For example, it may be desirable to activate the shield 60 early in the stroke such that the shield 60 is activated and advanced into contact with the patient's skin. Upon removal of the needle from the patient, the shield 60 simply slides completely to the extended position, automatically covering the needle 95 as it is withdrawn from the patient. Alternatively, the latch members 74 and/or plunger 98 may be configured to activate the shield 60 only upon complete depression of the plunger 98. In a further alternative, the plunger 98 may include a radial portion, such as a tab or an annular rib (not shown), at an intermediate location thereon. The radial portion may engage and deflect the latch members 75 during depression of the plunger 98, similar to the thumb pad 99 described above.

While the invention is susceptible to various modifications, and alternative forms, specific examples thereof have been shown in the drawings and are herein described in detail. It should be understood, however, that the invention is not limited to the particular forms or methods disclosed, but to the contrary, the invention is to cover all modifications, equivalents, and alternatives falling within the spirit and scope of the appended claims.

What is claimed is:
1. A needle guard for a medical cartridge, comprising:
a body having a proximal end, a distal end, and a cavity configured for receiving a medical cartridge; and
a plunger locking mechanism attachable to the proximal end of the body for preventing access to the contents of a medical cartridge received in the body, the plunger locking mechanism including a flange with an aperture formed on an edge of the flange that, when a medical cartridge is received within the cavity of the body, is configured to allow the plunger shaft to slide within the aperture, while preventing the plunger from being proximally removed from a cartridge barrel of a medical cartridge, and that is configured to laterally receive the plunger shaft;
wherein the plunger locking mechanism is attached to the proximal end of the body by mating at least one pair of opposing tab slots disposed on the proximal end of the body with at least one pair of opposing tabs disposed on the plunger locking mechanism.
2. A needle guard for a medical cartridge, comprising:
a body having a proximal end, a distal end, and a cavity configured for receiving a medical cartridge having a cartridge barrel and a plunger, the plunger comprising a plunger shaft slidable within the medical cartridge, wherein the medical cartridge is a syringe having a needle extending from the cartridge barrel, a shield configured to be slidably attached to the body between a retracted position for exposing the needle, and an extended position to substantially cover the needle; and a plunger locking mechanism attachable to the proximal end of the body, the plunger locking mechanism including an aperture formed on an edge of a flange that, when the medical cartridge is received within the cavity of the body, is configured to allow the plunger shaft to slide within the aperture, while preventing the plunger from being proximally removed from the cartridge barrel, and that is configured to laterally receive the plunger shaft;

wherein the plunger locking mechanism is attached to the proximal end of the body by mating at least one pair of opposing tab slots disposed on the proximal end of the body with at least one pair of opposing tabs disposed on the plunger locking mechanism.

3. The needle guard of claim 2, wherein the shield is biased to slide towards the extended position, and the cartridge has a needle.

4. The needle guard of claim 2, further comprising a frangible cap attached to the shield for preventing access to the needle prior to administration of a medical product and which cap will break if removed to indicate that tampering has occurred.

5. The needle guard of claim 4, wherein the proximal end of the body comprises a finger grip, and the plunger locking mechanism is attached to the finger grip.

6. A needle guard for syringes, comprising:
a body having a proximal end, a distal end, and a cavity configured for receiving a medical cartridge having a cartridge barrel and a plunger, the plunger comprising a plunger shaft slidable within the medical cartridge, a thumb pad on a proximal end of the shaft, a plunger flange on a distal end of the shaft, a tip extending from the plunger flange, and a piston coupled to the tip; and a plunger locking mechanism attachable to the proximal end of the body, the plunger locking mechanism including a member with an aperture that, when the medical cartridge is received within the cavity of the body, is configured to allow the plunger shaft to slide within the aperture, wherein the plunger flange being larger than the aperture and abutting the member thereby preventing the plunger from being removed from the cartridge barrel;

wherein the member is mountable to the proximal end of the body by mating at least one pair of opposing tab slots disposed on the proximal end of the body with at least one pair of opposing tabs disposed on the member.

7. The needle guard of claim 6, wherein the aperture is formed on an edge of the member, such that the plunger shaft can be laterally received within the aperture.

8. A needle guard for a syringe, comprising:
a body having a proximal end, a distal end, and a cavity being adapted to receive a medical cartridge having a cartridge barrel and a plunger, the plunger comprising a plunger shaft slidable within the medical cartridge, wherein the medical cartridge is a syringe that comprises a needle extending from the cartridge barrel, and further comprising a shield configured to be slidably attached to the body between a retracted position for exposing the needle, and an extended position for substantially covering the needle; and a plunger locking mechanism attached to the proximal end of the body, the plunger locking mechanism including a flange with an aperture formed on an edge of the flange to slidably laterally receive the plunger shaft, the flange with the aperture being configured for preventing the plunger from being proximally removed from the cartridge barrel;

wherein the plunger locking mechanism is attached to the proximal end of the body by mating at least one pair of opposing tab slots disposed on the proximal end of the body with at least one pair of opposing tabs disposed on the plunger locking mechanism.

9. The needle guard of claim 8, wherein the proximal end of the body comprises a finger grip, and the plunger locking mechanism is attachable to the finger grip.

10. The needle guard of claim 1, wherein the aperture is formed on the edge of the flange such that the flange has a C-shape.

* * * * *

UNITED STATES PATENT AND TRADEMARK OFFICE
CERTIFICATE OF CORRECTION

PATENT NO. : 9,550,027 B2
APPLICATION NO. : 14/108231
DATED : January 24, 2017
INVENTOR(S) : Lars Tommy Westbye It is certified that error appears in the above-identified patent and that said Letters Patent is hereby corrected as shown below:

In the Claims

Column 14, Line 27, Claim 8, after "to" delete "slidably"

Signed and Sealed this
Fourth Day of April, 2017

Michelle K. Lee
*Director of the United States Patent and Trademark Office*